US008398970B2

(12) United States Patent
Deitmer et al.

(10) Patent No.: US 8,398,970 B2
(45) Date of Patent: Mar. 19, 2013

(54) METHOD OF PREVENTING EARLY *LAWSONIA INTRACELLULARIS* INFECTIONS

(75) Inventors: Ricarda Deitmer, Gau-Algesheim (DE); Knut Elbers, Mittelbiberach (DE)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 151 days.

(21) Appl. No.: 12/678,361

(22) PCT Filed: Sep. 16, 2008

(86) PCT No.: PCT/EP2008/062315
§ 371 (c)(1),
(2), (4) Date: Jun. 8, 2010

(87) PCT Pub. No.: WO2009/037262
PCT Pub. Date: Mar. 26, 2009

(65) Prior Publication Data
US 2010/0266637 A1    Oct. 21, 2010

(30) Foreign Application Priority Data
Sep. 17, 2007 (EP) .................................. 07116528

(51) Int. Cl.
*A61K 48/00* (2006.01)
*A61K 39/02* (2006.01)
*A61K 39/00* (2006.01)

(52) U.S. Cl. .................. 424/93.2; 424/93.4; 424/234.1; 424/184.1; 424/825

(58) Field of Classification Search .................. None
See application file for complete search history.

(56) References Cited

U.S. PATENT DOCUMENTS

| | | |
|---|---|---|
| 3,479,430 A | 11/1969 | Welter |
| 3,907,987 A | 9/1975 | Wilson |
| 4,132,597 A | 1/1979 | Kvanta |
| 4,237,218 A | 12/1980 | Monthony et al. |
| 4,880,739 A | 11/1989 | Yamada et al. |
| 4,904,597 A | 2/1990 | Inoue et al. |
| 4,920,048 A | 4/1990 | Diderichsen |
| 5,126,265 A | 6/1992 | Cidaria et al. |
| 5,130,232 A | 7/1992 | Lee et al. |
| 5,192,679 A | 3/1993 | Dawson et al. |
| 5,230,912 A | 7/1993 | Yajima et al. |
| 5,296,221 A | 3/1994 | Mitsuoka et al. |
| 5,318,908 A | 6/1994 | Seki et al. |
| 5,338,670 A | 8/1994 | Sekura et al. |
| 5,380,657 A | 1/1995 | Schaefer et al. |
| 5,436,001 A | 7/1995 | Kramer |
| 5,610,059 A | 3/1997 | Joens et al. |
| 5,714,375 A | 2/1998 | Knittel et al. |
| 5,885,823 A | 3/1999 | Knittel et al. |
| 6,414,036 B1 | 7/2002 | Ninkov |
| 6,605,696 B1 | 8/2003 | Rosey |
| 6,649,660 B2 | 11/2003 | Ninkov |
| 6,921,536 B2 | 7/2005 | Jacobs et al. |
| 6,982,314 B2 | 1/2006 | Rosey |
| 7,022,328 B1 | 4/2006 | Panaccio et al. |
| 7,052,697 B1 | 5/2006 | Hasse et al. |
| 7,303,891 B2 | 12/2007 | Merza |
| 7,312,065 B2 | 12/2007 | Roof et al. |
| 7,550,270 B2 | 6/2009 | Kroll et al. |
| 7,635,590 B2 | 12/2009 | Merza |
| 7,758,870 B2 | 7/2010 | Roof et al. |
| 7,799,562 B2 | 9/2010 | Merza |
| 7,960,174 B2 | 6/2011 | Merza |
| 7,993,649 B1 | 8/2011 | Merza |
| 8,003,107 B1 | 8/2011 | Merza |
| 8,007,801 B1 | 8/2011 | Merza |
| 8,007,802 B1 | 8/2011 | Merza |
| 8,021,663 B2 | 9/2011 | Merza |
| 8,058,062 B1 | 11/2011 | Merza |
| 8,114,666 B2 | 2/2012 | Merza |
| 8,114,667 B2 | 2/2012 | Merza |
| 2002/0103261 A1 | 8/2002 | Ninkov |
| 2003/0021802 A1 | 1/2003 | Rosey |
| 2003/0087421 A1 | 5/2003 | Gebhart et al. |
| 2003/0157120 A1 | 8/2003 | Panaccio et al. |
| 2005/0031647 A1 | 2/2005 | Roof et al. |
| 2005/0069559 A1 | 3/2005 | Jacobs et al. |
| 2005/0143561 A1 | 6/2005 | Rosey |
| 2006/0024696 A1 | 2/2006 | Kapur et al. |

(Continued)

FOREIGN PATENT DOCUMENTS

| | | |
|---|---|---|
| EP | 1219711 A2 | 7/2002 |
| EP | 1403643 A1 | 3/2004 |

(Continued)

OTHER PUBLICATIONS

New Riverside University Dictionary, The Riverside Publishing Company, p. 933, 1984.*
Illustrated Stedman's Medical Dictionary, 24th Edition, Williams and Wilkins, London, p. 707, 1982.*
Kesl et al. American Association of Swine Veterinarians, 139-142, 2004.*
Remington's Pharmaceutical Sciences, (Ed) Gennaro AR. 18th Edition, Mack Publishing Company, Easton, Pennsylvania, Chapter 35, pp. 697-702, 1990.*
Armbruster, G., et al; Evaluation of Enterisol® Li Ileitis Vaccine and Tylan® Premix efficacy Against Porcine Proliferative Enteropathy in a Challenge Model; Proceedings of the 18th International Pig Veterinary Society (2004) vol. 2 p. 579.

(Continued)

*Primary Examiner* — S. Devi
(74) *Attorney, Agent, or Firm* — Michael P. Morris; Joyce L. Morrison

(57) ABSTRACT

The present invention relates inter alia to the use of a combination of a vaccine against *Lawsonia intracellularis* and an anti-*Lawsonia* antibiotic for the prevention or reduction of early, preferably fulminant *Lawsonia intracellularis* infections. The present invention relates particularly to the use of a live *Lawsonia intracellularis* vaccine in conjunction with an antibiotic that is effective against *Lawsonia intracellularis*, for the avoidance or reduction of early *Lawsonia intracellularis* infections in animals.

6 Claims, 1 Drawing Sheet

U.S. PATENT DOCUMENTS

| | | | |
|---|---|---|---|
| 2006/0171960 | A1 | 8/2006 | Chu et al. |
| 2006/0204522 | A1 | 9/2006 | Kroll et al. |
| 2006/0286118 | A1 | 12/2006 | Vermeij |
| 2007/0014815 | A1 | 1/2007 | Kroll et al. |
| 2007/0212373 | A1 | 9/2007 | Vermeij |
| 2008/0063648 | A1 | 3/2008 | Kroll |
| 2008/0112980 | A1 | 5/2008 | Roof et al. |
| 2008/0226669 | A1 | 9/2008 | Roof et al. |
| 2008/0241190 | A1 | 10/2008 | Kroll et al. |
| 2008/0279893 | A1 | 11/2008 | Vaughn et al. |
| 2009/0215698 | A1 | 8/2009 | Schaeffer et al. |
| 2010/0062021 | A1* | 3/2010 | Winkelman ............... 424/234.1 |
| 2010/0266637 | A1 | 10/2010 | Deitmer et al. |

FOREIGN PATENT DOCUMENTS

| | | |
|---|---|---|
| EP | 1586646 A2 | 10/2005 |
| WO | 9407531 A1 | 4/1994 |
| WO | 9639629 A1 | 12/1996 |
| WO | 9720050 A1 | 6/1997 |
| WO | 0189559 A2 | 11/2001 |
| WO | 0226250 A2 | 4/2002 |
| WO | 03003335 A1 | 1/2003 |
| WO | 03006665 A1 | 1/2003 |
| WO | 2004033631 A2 | 4/2004 |
| WO | 2005011731 A1 | 2/2005 |
| WO | 2005070958 A2 | 8/2005 |
| WO | 2006012949 A1 | 2/2006 |
| WO | 2006020730 A2 | 2/2006 |
| WO | 2006099561 A1 | 9/2006 |
| WO | 2006113782 A2 | 10/2006 |
| WO | 2006116763 A2 | 11/2006 |
| WO | 2007/011993 A1 | 1/2007 |
| WO | 2007140244 A2 | 12/2007 |
| WO | 2008063959 A1 | 5/2008 |
| WO | 2009037262 A2 | 3/2009 |

OTHER PUBLICATIONS

Bornhorn, R; Efficacy and Economical Impact of Oral Vaccination of Partially Infected piglets with Enterisol® Ileitis; Praktischer Tierartz (2007) vol. 88 No. 3 p. 172.

International Search Report for PCT/EP2008/062315 mailed Jun. 17, 2009.

Mcorist et al., "Control of porcine proliferative enteropathy by oral administration of chlortetracycline". The Veterinary Record, vol. 144, Jan. 1999, pp. 48-49.

Mcorist et al., "Early Lesions of Proliferative Enteritis in Pigs and Hamsters". Veterinary Pathology, vol. 26, No. 3, May 1989, pp. 260-264.

Mcorist et al., "Entry of the bacterium ileal symbiont intracellularis into cultured enterocytes and its subsequent release". Research in Veterinary Science, vol. 59, 1995, pp. 255-260.

Mcorist et al., "In Vitro and In-Life Studies of Efficacy of Valnemulin for Proliferative Enteropathy (Ileitis)". Proceedings of the 15th IPVS Congress, Birmingham, England, Jul. 1998, p. 114.

Mcorist et al., "In vitro testing of antimicrobial agents for proliferative enteropathy (ileitis)". Swine Health and Production, vol. 3, No. 4, Jul. and Aug. 1995, pp. 146-149.

Mcorist et al., "Monoclonal antibodies to intracellular campylobacter-like organisms of the porcine proliferative enteropathies". The Veterinary Record, vol. 121, No. 18, Oct. 1987, pp. 421-422.

Mcorist et al., "Oral administration of tylosin phosphate for treatment and prevention of proliferative enteropathy in pigs". Advanced Journal of Veterinary Research, vol. 58, No. 2, Feb. 1997, pp. 136-139.

Mcorist et al., "Polymerase chain reaction for diagnosis of porcine proliferative enteropathy". Veterinary Microbiology, vol. 41, No. 3, 1994, pp. 205-212.

Mcorist et al., "Porcine Proliferative Enteropathy". The Veterinary Record, vol. 132, No. 14, Apr. 1993, p. 368.

Mcorist et al., "Reproduction of Porcine Proliferative Enteropathy with Pure Cultures of Ileal Symbiont Intracellularis". Infection and Immunity, vol. 61, No. 10, Oct. 1993, pp. 4286-4292.

Mcorist et al., "Synergism of ileal symbiont intracellularis and gut bacteria in the reproduction of porcine proliferative enteropathy". The Veterinary Record, vol. 134, No. 13, Mar. 1994, pp. 331-332.

Mcorist et al., "The Treatment of Induced Porcine Proliferative Enteropathy (Ileitis) with Tylosin Tartrate (Tylan® Soluble, Elanco) Administered Via Drinking Water". Proceedings of the 15th IPVS Congress, Birmingham, England, Jul. 1998, p. 118.

Mcorist et al., "Treatment and prevention of porcine proliferative enteropathy with oral tiamulin". The Veterinary Record, vol. 139, Dec. 1996, pp. 615-618.

Nelson, J.B., "The Maternal Transmission of vaccinial Immunity in Swine". The Journal of Experimental Medicine, vol. 56, 1932, pp. 835-840.

Nelson, J.B., "The Maternal Transmission of Vaccinial Immunity in Swine". The Journal of Experimental Medicine, vol. 60, 1934, pp. 287-291.

Nielsen et al., ":The serological response to *Salmonella serovars* typhimurium and infantis in experimentally infected pigs. The time course followed with an indirect anti-LPS ELISA and bacteriological examinations". Veterinary Microbiology, vol. 47, 1995, pp. 205-218.

Oka et al., "Large-Scale Animal Cell Culture: A Biological Perspective". Large-Scale Mammalian Cell Culture, Marcel Dekker, Inc., New York and Basel, 1990, pp. 71-73.

Peace et al., "Comparative Analysis of the 16S rRNA Gene Sequence of the Putative Agent of Proliferative Ileitis of Hamsters". International Journal of Systematic Bacteriology, vol. 44, No. 4, Oct. 1994, pp. 832-835.

Pensaert et al., "Viremia and effect of fetal infection with porcine viruses with special reference to porcine circovirus 2 infection". Veterinary Microbiology, vol. 98, 2004, pp. 175-183.

Pozo et al., "Study of *Lawsonia Intracellularis*Infection in Breeding Stock and Suckling Pigs". Proceedings of the 17th IPVS Congress, Ames, Iowa, 2002, vol. 2, p. 205.

Product Insert for Enterisol Ileitis®, Boehringer Ingelheim Vetmedica, Inc., Jan. 2005, 2 pages.

Product Insert for Enterisol® SC-54, Boehringer Ingelheim Vetmedica, Inc., May 2003, 2 pages.

Reuveny, S., "Microcarrier Culture Systems". Bioprocess Technology, vol. 10, 1990, pp. 271-341.

Reuveny, S., "Microcarriers in Cell Culture Structure and Applications". Advances in Cell Culture, vol. 4, 1985, pp. 213-247.

Rowland et al., "Intestinal Adenomatosis in the Pig: Occurrence of a Bacterium in Affected Cells". Nature, vol. 243, Jun. 1973, p. 417.

Rowland et al., Porcine intestinal adenomatosis: A possible relationship with necrotic enteritis, regional ileitis and proliferative haemorrhagic enteropathy. Veterinary Records, vol. 97, 1975, pp. 178-180.

Schoeb et al., "Enterocecocolitis Associated with Intraepithelial Campylobacter-like Bacteria in Rabbits (*Oryctolagus cuniculus*)". Veterinary Pathology, vol. 27, 1990, pp. 73-80.

Schultheiss, P.C., "A Study of the Pathogenicity of Campylobacter Species in Swine". A Thesis Submitted to the Faculty of the Graduate School of the University of Minnesota, Jun. 1987, pp. 1-287.

Senk et al., "Proliferative typhlocolitis—the fifth form of the porcine intestinal adenomatosis complex". Proceedings, International Pig Veterinary Society, 11th Congress, Jul. 1-5, 1990, Lausanne, Switzerlandk, 1990, p. 113.

Spier et al., "Trypsinization of BHK 21 Monolayer Cells Grown in Two Large-Scale Unit Process Systems". Biotechnology and Bioengineering, vol. XIX, 1977, pp. 1735-1738.

Starek et al., "Sows Seropositive to *Lawsonia intracellularis* (LI) Influence Performance and LI Seropositivity of their Offspring". ACTA Veterinaria BRNO, vol. 73, No. 3, 2004, pp. 341-345.

Stills, H.F., "Isolation of an Intracellular Bacterium from Hamsters (*Mesocricetus auratus*) with Proliferative Ileitis and Reproduction of the Disease with a Pure Culture". Infection and Immunity, vol. 59, No. 9, Sep. 1991, pp. 3227-3236.

Tam et al., "Eukaryotic Cells Grown on Microcarrier Beads Offer a Cost-Efficient Way to Propagate *Chlamydia trachomatis*". BioTechniques, vol. 13, No. 3, 1992, pp. 374-378.

Thacker, E., "Vaccines How They Work, Why They Fail". National Hog Farmer, Apr. 15, 2003. Retrieved online Jun. 16, 2008, 6 pages. http://www.nationalhogfarmer.com/mag/farming_vaccines_work_why/index.html.

Tseneva et al., "Invasiveness and cytotoxicity as criteria in assessing Yersinia attenuation". Zhurnal Mikrobiologii, Epidemiologii, i Immunobiologii, vol. 10, No. 6, Sep. 1988, pp. 10-16, Abstract Only.

Walter et al., "Serologic profiling and vaccination timing for *Lawsonia intracellularis*". Journal of Swine Health and Production, vol. 12, No. 6, 2004, pp. 310-313.

Ward et al., "Diagnosing, treating, and controlling proliferative enteritis in swine". Veterinary Medicine, Food-Animal Practice, Mar. 1990, pp. 312-318.

Ward et al., "Reproduction of proliferative enteritis in pigs fed embryonated eggs inoculated with proliferative enteritis tissues". Proceedings, International Pig Veterinary Society, 11th Congress, Jul. 1-5, 1990, Lausanne, Switzerland, p. 116.

Wittmann et al., "Colostral Immunity in Piglets From Sows Vaccinated With Inactivated Aujeszky Disease Virus Vaccine". Archives of Virology, vol. 60, 1979, pp. 33-42.

Wiuff et al., "Immunochemical analyses of serum antibodies from pig herds in a *Salmonella* non-endemic region". Veterinary Microbiology, vol. 85, 2002, pp. 69-82.

Yates et al., "Proliferative Hemorrhagic Enteropathy in Swine: An Outbreak and Review of Literature". Canadian Veterinary Journal, vol. 20, Oct. 1979, pp. 261-268.

"Multicomponent Vaccine Development". NIH Guide, vol. 22, No. 28, Aug. 1993, Retrieved from URL: http://grants.nih.gov/grants/guide/rfa-files/RFA-AI-93-017.html, Retrieved on Nov. 20, 2006, 9 pages.

"Vaccination Guidelines for Swine". Vido Swine Technical Group, Jun. 2004, (obtained on Jan. 6, 2009 from http://www.vido.org/pdf/vstg_pubs/Vaccination%20Guidelines_SWINE_.june18.2004-tl1.pdf).

Alderton et al., "Experimental Reproduction of Porcine Proliferative Enteritis". Journal of Comparative Pathology, vol. 106, 1992, pp. 159-167.

Barna et al., "Effect of gilt seropositivity to *Lawsonia intracellularis* (LI) on their offspring's seropositivity to LI and on diarrhoea after a pure-culture challenge". Preventive Veterinary Medicine, vol. 61, No. 1, Sep. 2003, pp. 71-78.

Birch et al., "Suspension Culture of Mammalian Cells". Large-Scale Mammalian Cell Culture, Marcel Dekker, Inc., New York and Basel, 1990, pp. 258-270.

Boesen et al., "Development, characterization and diagnostic application of a monoclonal antibody specific for a proteinase K resistant *Lawsonia intracellularis* antigen". Veterinary Microbiology, vol. 105, 2006, pp. 199-206.

Boesen et al., "Evaluation of a novel enzyme-linked immunosorbent assay for serological diagnosis of porcine proliferative enteropathy". Veterinary Microbiology, vol. 109, 2005, pp. 105-112.

Boosinger et al., "Campylobacter sputorum subsp mucosalis and *Campylobacter hyointestinalis* infections in the intestine of gnotobiotic pigs". American Journal of Veterinary Research, vol. 46, No. 10, Oct. 1985, pp. 2152-2156.

Bouma et al., "The influence of maternal immunity on the development of the in vitro lymphocyte proliferation response against pseudorabies virus in pigs". Research in Veterinary Science, vol. 64, 1998, pp. 167-171.

Brock et. al., "Immunization for Infectious Disease". Biology of Microorganisms, Ch. 16, PrenticeHall, Inc., 4th Ed., (19), 1984, pp. 557-558.

Chang et al., "*Campylobacter hyointestinalis*, a possible cause of proliferative enteritis in swine". Campylobacter II. Proceedings of the Second International Workshop on *Campylobacter* Infections, Brussels, Sep. 6-9, 1983, p. 131.

Chang et al., "Immunofluorescent demonstration of *Campylobacter hyointestinalis* and *Campylobacter sputorum* subsp *mucosalis* in swine intestines with lesions of proliferative enteritis". American Journal of Veterinary Research, vol. 45, No. 4, Apr. 1984, pp. 703-710.

Desrosiers, R., "Experiences with the Use of Enterisol® Ileitis in Canadian Breeding Animals". Ileitis Symposium, Hamburg, Germany, Jun. 28, 2004, (obtained on Jan. 6, 2009 from http://www.animal-health-online.de/drms/Vortrag_Desrosiers.pdf) pp. 1-4.

Fattom et al., "Epitopic overload at the site of injection may result in suppression of the immune response to combined capsular polysaccharide conjugate vaccines". Vaccine, vol. 17, 1999, pp. 126-133.

Finn, D.L., "Isolation and characterization of viral agents associated with porcine proliferative enteritis". A Thesis Submitted to the faculty of the Department of Microbiology and Immunology in Partial Fulfillment of the Requirements for the Degree of Master of Science with a Major in Microbiology, The University of Arizona, 1987, pp. 1-86.

Finter et al., "Large-Scale Mammalian Cell Culture: A Perspective". Large-Scale Mammalian Cell Culture, Marcel Dekker, Inc., New York and Basel, 1990, pp. 1-14.

Fox et al., "*Campylobacter*-like Omega Intracellular Antigen in Proliferative Colitis of Ferrets". Laboratory Animal Science, vol. 38, No. 1, Feb. 1988, pp. 34-36.

Frey et al., "Coiled bodies contain U7 small nuclear RNA and associate with specific DNA sequences in interphase human cells". Proceedings of the National Academy of Sciences of the United States of America, vol. 92, No. 13, Jun. 1995, pp. 5915-5919.

Gebhart et al., "Cloned DNA Probes Specific for the Intracellular *Campylobacter*-Like Organism of Porcine Proliferative Enteritis". Journal of Clinical Microbiology, vol. 29, No. 5, May 1991, pp. 1011-1015.

Gebhart et al., "Ileal Symbiont Intracellularis, an Obligate Intracellular Bacterium of Porcine Intestines Showing a Relationship to *Desulfovibrio* Species". International Journal of Systematic Bacteriology, vol. 43, No. 3, Jul. 1993, pp. 533-538.

Gebhart et al., "Species-specific DNA probes for *Campylobacter* species isolated from pigs with proliferative enteritis". Veterinary Microbiology, vol. 24, 1990, pp. 367-379.

Griffiths, B., "Scaling-up of Animal Cell Cultures". Animal Cell Culture—A Practical Approach, Chapter 3, IRL Press Limited, Oxford, England, 1986, pp. 33-69.

Guedes et al., "Validation of an immunoperoxidase monolayer assay as a serologic test for porcine proliferative enteropathy". Journal of Veterinary Diagnostic Investigation, vol. 14, 2002, pp. 528-530.

Hancock et al., Modern Microbiological Methods, Bacterial Cell Surface Techniques, A Wiley-Interscience Publication, John Wiley & Sons, Chichester, 1988, pp. 90-91.

Holyoake et al., "Enzyme-linked immunosorbent assay for measuring ileal symbiont intracellularis-specific immunoglobulin G response in sera of pigs". Journal of Clinical Microbiology, vol. 32, No. 8, 1994, pp. 1980-1985.

Horin et al., "Polymorphisms in equine immune response genes and their associations with infections". Mammalian Genome, vol. 15, 2004, pp. 843-850.

International Search Report and Written Opinion for PCT/EP2008/062315 mailed Jun. 17, 2009.

Jasni et al., "Reproduction of proliferative enteritis in hamsters with a pure culture of porcine ileal symbiont intracellularis". Veterinary Microbiology, vol. 41, 1994, pp. 1-9.

Jones et al., "Enhanced Detection of Intracellular Organism of Swine Proliferative Enteritis, Ileal Symbiont Intracellularis, in Feces by Polymerase Chain Reaction". Journal of Clinical Microbiology, vol. 31, No. 10, Oct. 1993, pp. 2611-2615.

Jones, Gary F., "The Diagnosis and Cause of Swine Proliferative Enteritis"., A Thesis Submitted to the Faculty of the Graduate School of the University of Minnesota, Minneapolis, MN, Jun. 1993, pp. 1-190.

Knittel et al., "Evaluation of antemortem polymerase chain reaction and serologic methods for detection of *Lawsonia intracellularis*-exposed pigs". American Journal of Veterinary Research, vol. 59, No. 6, Jun. 1998, pp. 722-723, 725.

Koyama et al., "In Vitro Cultivation and Partial Characterization of *Lawsonia Intracellularis* from a Japanese Field Case of Porcine Proliferative Enteropathy". Proceedings of the 18th IPVS Congress, vol. 1, Hamburg, Germany, 2004, p. 307.

Kroll et al., "Efficacy of an Avirulent *Lawsonia intracellularis* Vaccine in Swine". Abstracts of the General Meeting of the American Society for Microbiology, vol. 101, Session No. 236/Z, Abstract Z-40, American Society for Microbiology 101st General Meeting, Orlando, FL, May 23, 2001, p. 747.

Kroll et al., "Evaluation of protective immunity in pigs following oral administration of an avirulent live vaccine of *Lawsonia intracellularis*". American Journal of Veterinary Research, vol. 65, No. 6, May 2004, pp. 559-565.

Kroll et al., "Lipopolysaccharide-Based Enzyme-Linked Immunosorbent Assay for Experimental Use in Detection of Antibodies to *Lawsonia intracellularis* in Pigs". Clinical and Diagnostic Laboratory Immunology, vol. 12, No. 6, Jun. 2005, pp. 693-699.

Kroll et al., "Maternal Immunity Associated with *Lawsonia* Intracellularis Exposure and Vaccination". Proceedings of the 18th IPVS Congress, Hamburg, Germany, vol. I, 2004, p. 255.

Kuan et al., "Production of Monoclonal Antibody That Recognizes the Lipopolysaccharide of a *Campylobacter*-Like Organism". Microbiology and Immunology, vol. 36, No. 8, 1992, pp. 791-801.

Lavoie et al., "Equine proliferative enteropathy: a cause of weight loss, colic, diarrhoea and hypoproteinaemia in foals on three breeding farms in Canada". Equine Veterinary Journal, vol. 32, No. 5, Sep. 2000, pp. 418-425, Abstract Only.

Lawson et al., "Attempts to Cultivate the *Campylobacter*-like Organism of the Proliferative Enteropathies". Association of Vet. Teachers and Research Workers, Apr. 1990, Abstract C50.

Lawson et al., "Infection of cultured rat enterocytes by Ileal symbiont intracellularis depends on host cell function and actin polymerisation". Veterinary Microbiology, vol. 45, 1995, pp. 339-350.

Lawson et al., "Intestinal Adenomatosis in the Pig: A Bacteriological Study"., Research Journal of Veterinary Sciences, vol. 37, 1974, pp. 331-336.

Lawson et al., "Intracellular Bacteria of Porcine Proliferative Enteropathy: Cultivation and Maintenance In Vitro". Journal of Clinical Microbiology, vol. 31, No. 5, May 1993, pp. 1136-1142.

Lawson et al., "Proliferative *Haemorrhagic enteropathy*". Research in Veterinary Science, vol. 27, 1979, pp. 46-51.

Lawson et al., "Review: Proliferative Enteropathy". Journal of Comparative Pathology, vol. 122, 2000, pp. 77-100.

Lomax et al., "Experimentally induced porcine proliferative enteritis in specific-pathogen-free pigs". American Journal of Veterinary Research, vol. 43, No. 9, Sep. 1982, pp. 1615-1621.

Lomax, L.G., "Porcine proliferative enteritis—characterization of the naturally occurring and experimental disease". A Dissertation Submitted to the Graduate Faculty in Partial Fulfillment of the Requirements for the Degree of Doctor of Philosophy. Iowa State Univeristy, Ames, Iowa, 1981, pp. 1-206.

Love et al., "Pathology of Proliferative *Haemorrhagic Enteropathy* in Pigs". Veterinary Pathology, vol. 16, 1979, pp. 41-48.

McCluskey et al., "LsaA, an Antigen Involved in Cell Attachment and Invasion, Is Expressed by *Lawsonia intracellularis* during Infection In Vitro and In Vivo". Infection and Immunity, vol. 70, No. 6, Jun. 2002, pp. 2899-2907.

Mcorist et al., "Antimicrobial Susceptibility of Ileal Symbiont Intracellularis Isolated from Pigs with Proliferative Enteropathy". Journal of Clinical Microbiology, vol. 33, No. 5, May 1995, pp. 1314-1317.

Mcorist et al., "Characterization of *Lawsonia intracellularis* gen. nov., sp. nov., the Obligately Intracellular Bacterium of Porcine Proliferative Enteropathy". International Journal of Systematic Bacteriology, vol. 45, No. 4, Oct. 1995, pp. 820-825.

\* cited by examiner

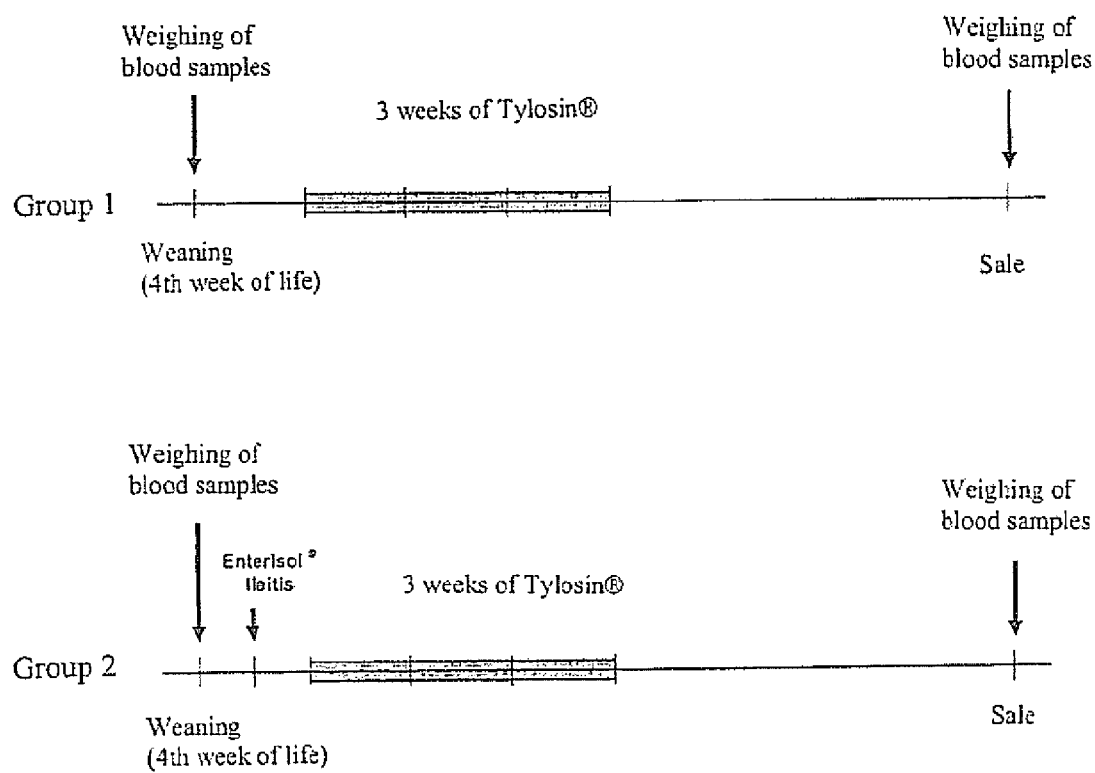

METHOD OF PREVENTING EARLY *LAWSONIA INTRACELLULARIS* INFECTIONS

This application is the national phase entry under 35 U.S.C. §371 of International Application No. PCT/EP2008/062315, filed Sep. 16, 2008, which claims priority to European Patent Application No. 07116528.6, filed Sep. 17, 2007, which are hereby incorporated by reference in their entireties.

TECHNICAL FIELD

The present invention relates to the field of medicine, particularly the field of infectious diseases. The present invention relates inter alfa to the use of a combination of a live vaccine against *Lawsonia intracellularis* and an anti-*Lawsonia* antibiotic for preventing or reducing early *Lawsonia intracellularis* infections.

BACKGROUND TO THE INVENTION

Porcine Proliferative Enteropathy (PPE, ileitis) is a disease of very great significance worldwide to the economics of pig production (Chouet et al. 2003, Wendt et al. 2006). The pathogen that causes the disease, *Lawsonia intracellularis* (L.i.), is spread through the faeces of the pigs and causes damage to the intestinal mucosa in the large and small bowel that is critical to the digestive function (Kroll et al. 2005).

For many years, different antibiotics have been licensed for the treatment of ileitis (=*Lawsonia intracellularis* infection). The active substances belong to the bacteriostatic antibiotics. They do not kill the pathogens directly but inhibit the multiplication of *Lawsonia intracellularis* (Armbuster et al. 2004, Busch et al. 2000, Collins et al. 2000a, Dritz et al. 2002, Kesl et al. 2004, Paradis 2004, Thaker and Bilkei 2006, Tzika et al. 2004, Veenhuizen et al. 1998a, Walter et al. 2000, Winkelman et al. 2000). For some years, a vaccine (Enterisol® Ileitis, made by Boehringer Ingelheim Vetmedica GmbH) has been available against the disease forms induced by *Lawsonia intracellularis*. The objective of the vaccination measures is to build up a reliable immunity before the first contact with the field pathogen. In order that the animals have developed a reliable immunity before the first field infection, the animals, particularly piglets, have to be vaccinated as early as possible, preferably in the first three weeks of life.

In Germany, a significant increase in clinical cases of ileitis has been observed in the last 12 months. This is due not least to the ban on antibiotic performance promoters that took effect on 1 Jan. 2006 (EC Regulation 1831, 2003). In addition, the number of farms that had infections occurring shortly after weaning (=removal from the mother sow) increased considerably. In these farms the question is how it is possible to meet the requirement of effectively vaccinating the piglets three weeks before the field infection.

In the prior art the combined administration of *Lawsonia intracellularis* vaccine and anti-*Lawsonia* antibiotic is described. For example, Armbruster et al. in 2006 describe a method in which 5-week-old piglets were vaccinated with *Lawsonia intracellularis* vaccine and 25 days after vaccination were treated with tylosin, an anti-*Lawsonia* antibiotic. However, such a treatment does not protect the animals from early and, in particular, early fulminant infections, such as are observed more and more frequently (Hardge et al. 2006, Steinheuer et al. 2007). On the one hand, the vaccination of the animals at 5 weeks old is carried out at a very late stage. On the other hand, the administration of tylosin from day 25 after vaccination is insufficient to prevent or alleviate corresponding early infections that occur during the period when the animals have not yet built up any reliable immunity. Besides Armbruster et al. 2004, Bornhorn 2007 also describes early attempts at a so-called embedded vaccination. Like the treatment plan used by Armbruster et al. 2004, the treatment plan described by Bornhorn is unable to prevent or alleviate early infections. The process described by Bornhorn is used to treat existing *Lawsonia intracellularis* infections.

The aim of the present invention was to provide a method of preventing or at least reducing early *Lawsonia intracellularis* infections.

A further aim of the present invention was to vaccinate animals successfully against *Lawsonia intracellularis* in spite of the early infection pressure caused by production methods.

A further aim of the present invention was to improve the general weight gain of animals, particularly animals for fattening, in spite of early infection with *Lawsonia intracellularis* caused by production methods.

These aims are achieved by the methods/uses described hereinafter.

DESCRIPTION OF THE FIGURES

FIG. 1: Description of the test

DESCRIPTION OF THE INVENTION

Before embarking on the embodiments of the invention it should be pointed out that the singular forms "a" and "an" used herein and in the appended claims also include references to the plural, unless the context indicates otherwise. Even if they are defined differently, all the technical and scientific terms used herein have the same meanings as in the general knowledge of a skilled man in the field of the invention. Although all the similar or corresponding methods and materials used herein can be used in practice or in the experiments of the invention, the preferred methods, apparatus and materials will now be described. All the publications mentioned are hereby incorporated by reference for the purpose of describing and disclosing the objects, methods and uses according to the invention which may be used in connection with the invention. This is not to be taken as an admission that the invention, as an earlier invention, could not claim precedence over such a disclosure.

DEFINITIONS

The term "live *Lawsonia intracellularis* vaccine" refers to a vaccine that contains live, non-inactivated *Lawsonia intracellularis* as immunogen. Preferably, the live, non-inactivated *Lawsonia intracellularis* bacteria are so-called attenuated bacteria, i.e. bacteria that are non-pathogenic to the host but are still immunogenic. Examples of corresponding bacteria, which are not to be taken in a restrictive capacity, include inter alia the *Lawsonia intracellularis* bacteria described in WO-A-96/39629 and WO 2005-A-011731 which are numbered PTA 4926 or ATCC 55783, deposited for patent law purposes at the "American. Type Culture Collection" (ATCC) 10801 University Boulevard, Manassas, Va. 20110-2209.

By a "vaccine" is meant a pharmaceutical composition that contains at least one immunogen for immunising animals.

The skilled man understands the term "immunogen" to mean a substance that can trigger an immune response in an animal, directed against the corresponding immunogen or a pathogen that contains this immunogen.

The expression "reduction of early *Lawsonia intracellularis* infections" means for the purposes of the present invention that the number of animals detectably infected with *Law-* sonia intracellularis which have been treated by the method according to the invention is reduced by more than 20%, preferably more than 30%, more preferably more than 50%, still more preferably more than 70% compared with a control group of animals that have not been treated accordingly.

The term "detectably" or "detectable infection" means for the purposes of the present invention that the infection with Lawsonia intracellularis can be detected by standard methods such as for example antibody detection tests, antigen detection tests or polymerase chain reaction (PCR) tests. Corresponding tests are described by way of example in Keller et al. (2004) and Suh et al. (2000). The tests described therein are used within the scope of the present patent application as a reference test to detect Lawsonia intracellularis infection beyond any doubt.

The term "early infection" for the purposes of the present invention means a Lawsonia intracellularis infection acquired within the first 6 weeks of life, preferably within the first 8 weeks of life, more preferably within the first 10 weeks of life and still more preferably within the first 12 weeks of life of the animals.

The term "fulminant infection" means a Lawsonia intracellularis infection in which the infected animal is excreting Lawsonia intracellularis bacteria, for example through its faeces. The excretion of bacteria can be detected for example with a polymerase chain reaction (PCR) test, as described for example in Suh et al. (2000), or an antigen detecting test, as described for example in Keller et al. (2004).

The term "early fulminant infection" means a Lawsonia intracellularis infection in which the infected animal excretes Lawsonia intracellularis bacteria within the first 6 weeks of life, preferably within the first 8 weeks of life, more preferably within the first 10 weeks of life and still more preferably within the first 12 weeks of life of the animals, for example through the faeces. The excretion of bacteria can be detected by a polymerase chain reaction (PCR) test, as described for example in Suh et al. (2000) or an antibody detection test, as described for example in Keller et al. (2004).

The phrase "until Lawsonia-specific antibodies are detected" refers to the change in the immune status of a animal from "antibody-negative" to "antibody-positive" as the result of an active vaccination with a vaccine against Lawsonia intracellularis. An animal is deemed to be "antibody-negative" if a serum sample from a vaccinated animal reacts negatively in the antibody test described by Keller et al. (2004). An animal is deemed to be "antibody-positive" if two independent serum samples from the animal react positively in the antibody test described by Keller et al. (2004). In particular an animal is deemed to be "antibody-positive" if the corresponding antibodies can be detected in serum dilutions of 1:4, preferably 1:16, more preferably 1:32, still more preferably 1:64 in the antibody test described by Keller et al. (2004). In other words, the phrase "until Lawsonia-specific antibodies are detected" in the context of the present invention represents the acquisition of Lawsonia intracellularis-specific antibodies, particularly the acquisition of reliable immunity from infections with Lawsonia intracellularis.

The term "reliable immunity" is used in the context of the present invention if an animal vaccinated against Lawsonia intracellularis does not develop an early fulminant Lawsonia intracellularis infection, Reliable immunity can both be conferred by antibodies and based on a cellular immune response.

The term "anti-Lawsonia antibiotic" means an agent that is capable of inhibiting the multiplication of Lawsonia intracellularis bacteria. This inhibition is present if, following the administration of a corresponding anti-Lawsonia agent, Lawsonia intracellularis bacteria grow more slowly in vivo or in vitro by more than a factor 2, preferably by more than a factor 5, more preferably by more than a factor 10, still more preferably by more than a factor 50 than Lawsonia intracellularis bacteria that have been grown under the same conditions, but without the administration of the corresponding anti-Lawsonia antibiotic. The reduced growth can be determined for example by means of the number of Lawsonia intracellularis bacteria in a culture. There is growth inhibition if a culture treated with anti-Lawsonia antibiotics contains only 50%, preferably only 20%, still more preferably only 10%, still more preferably only 2% Lawsonia intracellularis bacteria by comparison with an untreated culture at a specific stage of the cultivation, preferably after 4 days of in vitro cultivation. It will be self-evident to the skilled man that he should use the antibiotic in question in a dosage range adapted to its specific activity. This range can be ascertained by simple titration tests. An anti-Lawsonia antibiotic is any antibiotic that can bring about the inhibition described above; it need not be registered and licensed for the treatment of Lawsonia intracellularis. Anti-Lawsonia antibiotics and methods of using them are described by way of example inter alia in Armbuster et al. 2004, Busch et al. 2000, Collins et al. 2000a, Dritz et al. 2002, Kesl et al. 2004, Paradis 2004, Thaker and Bilkei 2006, Tzika et al. 2004, Veenhuizen et al. 1998a, Walter et al. 2000, Winkelman et al. 2000, the anti-Lawsonia antibiotics and methods of using them described therein being purely examples that should not be taken as definitive. Examples of anti-Lawsonia antibiotics include acetylisovaleryltylosin, tulathromycin (Draxxin), lincospectin, tiamulin, tylosin, valnemulin.

The term "animal" refers to fish, birds and mammals such as for example pigs, horses, mice, dogs, cats, preferably pigs. The term animal refers in particular to the corresponding young, preferably young pigs (=piglets).

DETAILED DESCRIPTION OF THE INVENTION

The aim of the present invention was to provide a process that can successfully effectively vaccinate and protect young animals, preferably piglets, against corresponding early infections with Lawsonia intracellularis in spite of production-related early infections. For this, the animals are vaccinated as early as possible and the field pathogen pressure is suppressed by treatment with anti-Lawsonia antibiotics until the young animals, particularly piglets, have built up a reliable immunity as a result of the vaccination.

Consequently, the present invention relates to the use of a live Lawsonia intracellularis vaccine in combination with an anti-Lawsonia antibiotic for the prevention or reduction of early Lawsonia intracellularis infections in animals, characterised in that the Lawsonia intracellularis vaccine is administered within the first four (4) weeks of life and the antibiotic is administered from day three (3) after the administration of the Lawsonia intracellularis vaccine to the animals. A corresponding treatment plan is referred to as "early embedded immunisation" or "early embedded vaccination".

According to a particular embodiment the early infection is a fulminant infection, i.e. According to the above definition an infection with excretion of pathogens. According to another embodiment the Lawsonia intracellularis vaccine is administered within the first three (3) weeks of life of the animals. A corresponding method is described inter alia in the International Patent Application WO-A-2007/011993. According to another embodiment the Lawsonia intracellularis vaccine is administered between day 1 and day 21, preferably between day 1 and day 20, preferably between day 1 and day 19, preferably between day 1 and day 18, preferably between day 1 and day 17, preferably between day 1 and day 16, preferably between day 1 and day 15, preferably between day 1 and day 14, preferably between day 1 and day 13, preferably between day 1 and day 12, preferably between day 1 and day 11, preferably between day 1 and day 10, preferably between day 1 and day 9, preferably between day 1 and day 8, preferably between day 1 and day 7, preferably between day 1 and day 6, preferably between day 1 and day 5, preferably between day 1 and day 4, preferably between day 1 and day 3, preferably on day 1 or day 2 after birth, most preferably on the day of birth. Surprisingly, it has been found that animals can be vaccinated with a live vaccine against Lawsonia intracellularis even in the presence of passively acquired anti-Lawsonia intracellularis antibodies. Corresponding findings are described inter alia in International Patent Application PCT/US200769646. However, passively acquired temporary immunity of this kind does not constitute lasting protection from early Lawsonia intracellularis infections, as demonstrated by the significant increase particularly in early clinical cases of ileitis caused by Lawsonia intracellularis.

Suitable live Lawsonia intracellularis vaccines are any of the corresponding live vaccines with live Lawsonia intracellularis bacteria, particularly the one that contains the Lawsonia intracellularis bacteria described in WO-A-96/39629 and WO 2005-A-011731 deposited at the ATCC under numbers PTA 4926 or ATCC 55783. Also suitable are those bacteria that have the same immunogenic properties as the deposited bacteria mentioned above. The live vaccine sold by Boehringer Ingelheim Vetmedica (Ingelheim am Rhein, Germany) under the brand name Enterisol® Ileitis has proved particularly effective.

A strain or isolate has the immunogenic properties of at least one of the deposited strains of bacteria mentioned above, provided that it reacts with one of the following antibodies: 301:39, 287:6, 268:29, 110:9, 113:2 or 268:18, which were deposited in connection with International Patent Application WO-A-2006/12949 for patent purposes in accordance with the Budapest Agreement (see below). Preferably, the detection test is a "sandwich ELISA" as described by way of example in Examples 2 and 3 of the above-mentioned International Patent Application WO-A-2006/12949, the antibody 110:9 being used as a so-called "catching antibody" and antibody 268:29 being used as a conjugated antibody. All the antibodies from WO-A-2006/12949 are produced in hybridoma cells that were deposited at the "Centre for Applied Microbiology and Research" (CAMR) and European Collection of Cell Cultures (ECACC)", Salisbury, Wiltshire SP4 0JG, UK, for patent purposes in accordance with the Budapest Agreement with effect from 11 May 2004. HYBRIDOMA CELL LINE 110:9 was successfully deposited with the accession number ECACC Acc. No. 04092204. HYBRIDOMA CELL LINE 113:2 was successfully deposited with the accession number ECACC Ace. No. 04092201. HYBRIDOMA CELL LINE 268:18 was successfully deposited with the accession number ECACC Acc. No. 04092202. HYBRIDOMA CELL LINE 268:29 was successfully deposited with the accession number ECACC Ace. No. 04092206. HYBRIDOMA CELL LINE 287:6 was successfully deposited with the accession number ECACC Acc. No. 04092203. HYBRIDOMA CELL LINE 301:39 was successfully deposited with the accession number ECACC Ace. No. 04092205.

The anti-Lawsonia antibiotic is preferably administered three (3) days after the vaccination with the live Lawsonia intracellularis vaccine or according to another embodiment from day 3 or day 4 after the vaccination with the live Lawsonia intracellularis vaccine for a specific length of time. Parallel administration should be avoided, in order to avoid a negative effect on the vaccine bacteria by the anti-Lawsonia antibiotic which might jeopardise the success of the vaccination.

According to another embodiment the anti-Lawsonia antibiotic is administered starting on day 3, 4, 5, 6 or 7, preferably starting on day 3, 4, 5 or 6, more preferably starting on day 3, 4 or 5, still more preferably on day 3 or day 4 after the administration of the Lawsonia intracellularis live vaccine to the animals over a specific period.

Consequently in another embodiment the present invention relates to the use of a live Lawsonia intracellularis vaccine in conjunction with an anti-Lawsonia antibiotic for preventing or reducing early, preferably fulminant Lawsonia intracellularis infections in animals, characterised in that the Lawsonia intracellularis vaccine is administered within the first four (4) weeks of life and the anti-Lawsonia antibiotic is administered starting on day 3, 4, 5, 6 or 7, preferably starting on day 3, 4, 5 or 6, more preferably starting on day 3, 4 or 5, still more preferably on day 3 or day 4 after the administration of the Lawsonia intracellularis live vaccine to the animals over a specific period. Preferably the vaccination of the animals with the live Lawsonia intracellularis vaccine is carried out within the first three (3) weeks of life or as mentioned above, preferably between day 1 and 21 after birth, more preferably between day 1 and 20 after birth etc.

The anti-Lawsonia antibiotic should be administered from day 3 after the vaccination at least until Lawsonia-specific antibodies are detected, in order to prevent early, preferably fulminant Lawsonia intracellularis infections. Numerous tests on pigs have shown that the infection time for Lawsonia intracellularis is between the 7th and 10th week of life (Hardge et al. 2006, Steinheuer et al. 2007). Moreover, the proportion of detected Lawsonia intracellularis infections increases after weaning.

Consequently according to another embodiment the present invention relates to the use of a live Lawsonia intracellularis vaccine in conjunction with an anti-Lawsonia antibiotic, for preventing or reducing early, preferably fulminant Lawsonia intracellularis infections in animals, characterised in that the Lawsonia intracellularis vaccine is administered within the first four (4) weeks of life, and the anti-Lawsonia antibiotic is given to the animals from day 3 after the administration of the Lawsonia intracellularis vaccine at least until Lawsonia-specific antibodies are detected.

Preferably the vaccination of the animals with the Lawsonia intracellularis live vaccine takes place within the first three (3) weeks of life, or as mentioned above preferably between day 1 and 21 after birth, more preferably between day 1 and 20 after birth etc. The administration of the anti-Lawsonia antibiotic starts on day 3, 4, 5, 6 or 7, preferably on day 3, 4, 5 or 6, more preferably on day 3, 4 or 5, still more preferably on day 3 or day 4 after the administration of the live Lawsonia intracellularis vaccine at least until reliable immunity is detected, preferably until Lawsonia-specific antibodies are detected in the vaccinated animals.

Young animals generally have passively acquired immunity to Lawsonia intracellularis infections while they are still suckling. The corresponding Lawsonia intracellularis specific antibodies are generally absorbed by the young animal through the colostrum from its mother, that has either been vaccinated against Lawsonia intracellularis and/or is seropositive with regard to Lawsonia intracellularis antibody as a result of a field infection. This passively acquired immunity, however, generally protects the young animal from early, preferably early fulminant Lawsonia intracellularis infections only during the suckling stage up to the time of weaning.

If vaccination takes place during the suckling period, i.e. before weaning, treatment with an anti-*Lawsonia* antibiotic is not absolutely essential. If there is a high infection pressure, it is advisable to give antibiotics during the suckling period as well. When the animal is weaned, there is a sudden jump in the risk of infection, at least until the animal has built up reliable immunity to *Lawsonia intracellularis* following the active vaccination against *Lawsonia intracellularis*.

Consequently, according to another embodiment, the present invention relates to the use of a live *Lawsonia intracellularis* vaccine in conjunction with an anti-*Lawsonia* antibiotic for preventing or reducing early, preferably fulminant *Lawsonia intracellularis* infections in animals, characterised in that the *Lawsonia intracellularis* vaccine is administered to young sucklings and the anti-*Lawsonia* antibiotic is administered after the weaning of the young animals (sucklings) at least until reliable immunity is detected, preferably until *Lawsonia*-specific antibodies are detected in the vaccinated animals. The vaccination of the sucklings takes place preferably between day 1 and day 21, preferably between day 1 and day 20, preferably between day 1 and day 19, preferably between day 1 and day 18, preferably between day 1 and day 17, preferably between day 1 and day 16, preferably between day 1 and day 15, preferably between day 1 and day 14, preferably between day 1 and day 13, preferably between day 1 and day 12, preferably between day 1 and day 11, preferably between day 1 and day 10, preferably between day 1 and day 9, preferably between day 1 and day 8, preferably between day 1 and day 7, preferably between day 1 and day 6, preferably between day 1 and day 5, preferably between day 1 and day 4, preferably between day 1 and day 3, preferably on day 1 or day 2 after birth, most preferably on the day of birth.

Reliable immunity to *Lawsonia intracellularis*, preferably by *Lawsonia*-specific antibodies usually sets in as a result of active vaccination against *Lawsonia intracellularis* about three (3) weeks after the vaccination.

Consequently, according to another embodiment by way of example, the present invention relates to the use of a live *Lawsonia intracellularis* vaccine in conjunction with an anti-*Lawsonia* antibiotic for preventing or reducing early, preferably fulminant *Lawsonia intracellularis* infections in animals, characterised in that the *Lawsonia intracellularis* vaccine is administered within the first four (4) weeks of life and the anti-*Lawsonia* antibiotic from day 3 after the administration of the *Lawsonia intracellularis* vaccine over a period of 1 to 21 days. Preferably the anti-*Lawsonia* antibiotic is administered over a period of 14 to 20 days, more preferably over a period of 15 to 19 days, more preferably over a period of 16 to 18 days. However, it is also possible to administer the anti-*Lawsonia* antibiotic over a period of more than 21 days, the preferred embodiment comprising administration over a period of 12 to 21 days as described above. It should be mentioned, in connection with this, that the administration of the anti-*Lawsonia* antibiotic preferably begins between day 3 and day 7, preferably between day 3 and day 6, more preferably between day 4 and day 5, still more preferably on day 3 or day 4 after the administration of the live *Lawsonia intracellularis* vaccine. The vaccination of the animals with the live *Lawsonia intracellularis* vaccine preferably takes place within the first three (3) weeks of life, or as mentioned above preferably between day 1 and 21 after birth, more preferably between day 1 and 20 after birth etc. If the vaccination takes place during the suckling phase, i.e. before the young animals are weaned, the anti-*Lawsonia* antibiotic is administered starting on the day of weaning, or within two (2) days after weaning up to day 21 after the vaccination, preferably up to day 18 after the vaccination.

According to another embodiment the anti-*Lawsonia* antibiotics can also be administered immediately after birth, or during the suckling phase. When using a live *Lawsonia intracellularis* vaccine it is important that the administration of the anti-*Lawsonia* antibiotic is interrupted not later than 2, preferably not later than 3, more preferably not later than 4 days before the vaccination with the live *Lawsonia intracellularis* vaccine. Consequently according to another embodiment by way of example the present invention relates to the use of a live *Lawsonia intracellularis* vaccine in conjunction with an anti-*Lawsonia* antibiotic for preventing or reducing early, preferably fulminant *Lawsonia intracellularis* infections in animals, characterised in that the *Lawsonia intracellularis* vaccine is administered within the first four (4) weeks of life and the anti-*Lawsonia* antibiotic is administered at most up to day 2, preferably at most up to day 3, more preferably at most up to day 4 before the administration of the live *Lawsonia intracellularis* vaccine and does not resume until day 3, 4, 5, 6 or 7, preferably day 3, 4, 5 or 6, more preferably day 3, 4 or 5, still more preferably on day 3 or day 4 after the administration of the *Lawsonia intracellularis* vaccine, preferably over a period of 1 to 21 days. Preferably, also, the anti-*Lawsonia* antibiotic is administered over a period of 14 to 20 days, more preferably over a period of 15 to 19 days, more preferably over a period of 16 to 18 days. However, it is also possible to administer the anti-*Lawsonia* antibiotic over a period of more than 21 days, the preferred embodiment being administration over a period of 12 to 21 days as described above.

The anti-*Lawsonia* antibiotic used may be, among others, the antibiotics mentioned earlier, namely acetylisovaleryltylosin, lincospectin, tiamulin, tulathromycin (draxxin), tylosin, valnemulin. According to a preferred embodiment the anti-*Lawsonia* antibiotic is: acetylisovaleryltylosin, lincospectin, tiamulin, tulathromycin (draxxin), tylosin or valnemulin, or a combination thereof. It is particularly preferred to use tylosin, preferably in an amount of 10 to 50 mg/kg of body weight of the animal.

Consequently another embodiment of the present invention relates to the use of a live *Lawsonia intracellularis* vaccine in conjunction with an anti-*Lawsonia* antibiotic for preventing or reducing early, preferably fulminant *Lawsonia intracellularis* infections in animals, as described above, characterised in that the anti-*Lawsonia* antibiotic is tylosin, which is preferably administered in an amount of 10 to 50 mg/kg of body weight of the animal. It should be mentioned, in connection with this, that the administration of the anti-*Lawsonia* antibiotic preferably starts between day 3 and day 7, preferably between day 3 and day 6, more preferably between day 3 and day 5, still more preferably on day 3 or day 4 after the administration of the live *Lawsonia intracellularis* vaccine, and tylosin is preferably administered over a period of 14 to 21 days, more preferably over a period of 15 to 19 days, more preferably over a period of 16 to 18 days.

According to another embodiment the present invention also relates to methods of preventing or reducing early, particularly fulminant *Lawsonia intracellularis* infections in animals, comprising administering a live *Lawsonia intracellularis* vaccine and an anti-*Lawsonia* antibiotic, characterised in that the *Lawsonia intracellularis* vaccine is administered within the first four (4) weeks of life and the anti-*Lawsonia* antibiotic is administered from day 3 after the administration of the *Lawsonia intracellularis* vaccine over a period of 12 to 2.1 days.

Preferably the anti-*Lawsonia* antibiotic is administered over a period of 14 to 20 days, more preferably over a period of 15 to 19 days, more preferably over a period of 16 to 18 days. However, it is also possible to administer the anti-*Lawsonia* antibiotic over periods of more than 21 days, the preferred embodiment comprising administration over a period of 12 to 21 days, as described above. It should be mentioned, in connection with this, that the administration of the anti-*Lawsonia* antibiotic is preferably started between day 3 and day 7, more preferably between day 3 and day 6, still more preferably between day 3 and day 5 and still more preferably on day 3 or day 4 after the administration of the live *Lawsonia intracellularis* vaccine. The vaccination of the animals with the live *Lawsonia intracellularis* vaccine is preferably carried out within the first three (3) weeks of life or, as mentioned above, preferably between day 1 and 21 after birth, more preferably between day 1 and 20 after birth etc.

The use according to the invention of a live *Lawsonia intracellularis* vaccine in conjunction with an anti-*Lawsonia* antibiotic as described here leads to a general improvement in the animals' state of health, particularly an improved weight gain by comparison with unvaccinated animals or those treated only with antibiotics. The study on which the invention is based led to a weight gain which was improved by more than 1 kg within the first 50 days after administration of the vaccine, or within the first 80, preferably the first 70 days of life.

Consequently according to another embodiment the present invention relates to the use of a live *Lawsonia intracellularis* vaccine in conjunction with an anti-*Lawsonia* antibiotic for improving the weight gain of animals, characterised in that the *Lawsonia intracellularis* vaccine is administered to the animals within the first four (4) weeks of life and the antibiotic is administered from day 3 after the administration of the *Lawsonia intracellularis* vaccine.

The improved weight gain is achieved particularly by avoiding or reducing early, preferably fulminant *Lawsonia intracellularis* infections in animals. According to a preferred embodiment of the present invention the improved weight gain in the first 50 days of life after vaccination is at least 1 kg, more preferably at least 1.5 kg. It should be mentioned, in connection with this, that the administration of the anti-*Lawsonia* antibiotic is preferably started between day 3 and day 7, more preferably between day 3 and day 6, still more preferably between day 3 and day 5 and still more preferably on day 3 or day 4 after the administration of the live *Lawsonia intracellularis* vaccine and it is preferably given over a period of 14 to 21 days, more preferably over a period of 15 to 19 days, still more preferably over a period of 16 to 18 days. The vaccination of the animals with the live *Lawsonia intracellularis* vaccine takes place according to a preferred embodiment within the first three (3) weeks of life, or as mentioned above preferably between day 1 and 21 after birth, more preferably between day 1 and 20 after birth etc.

The present invention is not restricted to the use of an anti-*Lawsonia* antibiotic in conjunction with a live vaccine against *Lawsonia intracellularis* for the prevention or reduction of early, particularly fulminant *Lawsonia intracellularis* infections. Rather, in a general aspect, the present invention also relates to the use of an anti-*Lawsonia* antibiotic in conjunction with any desired *Lawsonia intracellularis* vaccine, including an inactivated dead vaccine or a subunit vaccine, for example a recombinant peptide vaccine or an antigen preparation of *Lawsonia intracellularis* for the prevention or reduction of early, preferably fulminant *Lawsonia intracellularis* infections in animals, characterised in that the animals are vaccinated within the first four (4) weeks of life with the *Lawsonia intracellularis* vaccine and the anti-*Lawsonia* antibiotic is administered from the day of administration of the *Lawsonia intracellularis* vaccine until *Lawsonia*-specific antibodies are detected in the vaccinated animals. Preferably the antibiotics are given until a reliable immunity is built up against early, preferably fulminant *Lawsonia intracellularis* infections. Corresponding antibodies are generally formed within three weeks of vaccination. Therefore, according to another embodiment, the anti-*Lawsonia* antibiotic is administered over a period of 12 to 21 days. According to a preferred embodiment the anti-*Lawsonia* antibiotic is administered over a period of 14 to 20 days, more preferably over a period of 15 to 19 days, more preferably over a period of 16 to 18 days. It is also possible to administer the anti-*Lawsonia* antibiotic over a period of more than 21 days, the preferred embodiment being administration over a period of 12 to 21 days, as described above. The crucial point is that the anti-*Lawsonia* antibiotic is administered until the animal vaccinated with *Lawsonia intracellularis* vaccine has acquired reliable immunity to early, preferably fulminant *Lawsonia intracellularis* infections.

If the vaccination with the *Lawsonia intracellularis* vaccine starts only after the young animals have been weaned, the administration of the antibiotics may begin even before the administration of the *Lawsonia intracellularis* vaccine, provided that it is not a live vaccine. Thus, in another aspect, the present invention relates to the use of an anti-*Lawsonia* antibiotic in conjunction with a *Lawsonia intracellularis* vaccine, preferably an inactivated dead vaccine or a subunit vaccine, for example a recombinant peptide vaccine or an antigen preparation of *Lawsonia intracellularis*, for the prevention or reduction of early, preferably fulminant *Lawsonia intracellularis* infections in animals, characterised in that the animals are vaccinated within the first four (4) weeks of life with the *Lawsonia intracellularis* vaccine, preferably after weaning, and the anti-*Lawsonia* antibiotic is administered not later than from the day of weaning until *Lawsonia*-specific antibodies are detected in the vaccinated animals. Preferably the anti-*Lawsonia* antibiotic is administered over a period of up to 21 days after administration of the *Lawsonia intracellularis* vaccine, more preferably over a period of 12 to 21 days, still more preferably over a period of 14 to 20 days, still more preferably over a period of 15 to 19 days, still more preferably over a period of 16 to 18 days after administration of the *Lawsonia intracellularis* vaccine.

According to a preferred embodiment the vaccination of the animals with the *Lawsonia intracellularis* vaccine generally takes place within the first three (3) weeks of life or, as mentioned above, preferably between day 1 and 21 after birth, more preferably between day 1 and 20 after birth etc.

Suitable *Lawsonia intracellularis* antigens or immunogens for use as or in a subunit vaccine against *Lawsonia intracellularis* are described for example in. EP 1219711; U.S. Pat. No. 6,605,696; WO 96/39629; WO 97/20050; WO 00/69903; WO 00/69904; WO 00/69905; WO 00/69906; WO 02/38594; WO 02/26250; WO 03/006665; WO 04/033631; WO 05/026200; WO 05/011731; WO 06/113782; or WO 06/116763. Normally, a corresponding subunit vaccine has a content of antigen/immunogen of at least 2 µg per dose of vaccine, preferably between 2 and 500 µg per dose of vaccine. Corresponding subunit vaccines may be prepared by standard methods, for example by recombinant production in bacterial, yeast, insect cell or mammalian cell expression systems. The corresponding subunit vaccines are administered conventionally by parenteral route, for example by intramuscular or subcutaneous route. If a second vaccination is required to build up a reliable immunity, the anti-*Lawsonia* antibiotics are administered until the reliable immunity has been acquired. In individual cases this may take longer than the treatment period of 21 days.

The present uses/methods can be applied to the animals capable of being infected with *Lawsonia intracellularis*. These include, in particular, fish, birds and mammals, for example pigs, horses, dogs, cats, cattle. Preferably the methods/uses according to the invention are methods/uses for the prevention or reduction of early *Lawsonia intracellularis* infections, particularly early fulminant *Lawsonia intracellularis* infections in pigs.

EXAMPLES

The Examples that follow serve to further illustrate the objects/methods/uses according to the invention, without restricting them to the corresponding Examples.

Example 1

Embedded Early Vaccination with a *Lawsonia intracellularis* Vaccine

Equipment & Methods:

The study was carried out in a unit in North Rhine Westphalia with 160 sows and 600 breeding stalls, producing to a weekly cycle with four weeks' suckling. The piglets are sold on for fattening once they reach about 30 kg.

The unit was chosen because clinical ileitis occurred in the rearing quarters of the unit if the animals were not treated with an antibiotic effective against *Lawsonia intracellularis* for 10 days from the weaning time onwards. More detailed diagnosis found. *Lawsonia intracellularis* in the faeces of the clinically sick animals and other diarrhea-causing pathogens were ruled out.

The time frame of the study is shown in FIG. 1. Within the course of the study all the piglets were weighed on removal from the sows and individually marked with progressive numbering using an ear tag. A blood sample was taken from each of 15 piglets in each group of weaned animals on the day of removal from the sow and this blood was tested for antibodies to *Lawsonia intracellularis*. The weaned piglets were put into pens in groups of 10 animals. Four days after weaning every second group of weaned animals was vaccinated with Enterisol® Ileitis (Boehringer Ingelheim) in accordance with the manufacturer's instructions through the drinking water in their trough. The other groups remained unvaccinated. After 3 days without antibiotics following the ileitis vaccination, the piglets of all the weaned groups were subjected to tylosin therapy (10 mg/kg KGW Tylae G 25, Elanco Animal Health) for 18 days starting from the 8th day after weaning. The unvaccinated weaned piglets were also treated with tylosin in the same dosage for 18 days starting from the 8th day after weaning.

This 18-day therapy was significantly longer than the treatment period of 10 days that was previously in established use in the unit and which had already led to an apparently sufficient degree of clinical success. On the day of release from their pens, all the piglets were again weighed individually. In addition, blood samples were taken from 10 piglets in each market batch, and the samples were examined for antibodies to *Lawsonia intracellularis* using ELISA. All the study groups were subjected to identical care and feed conditions. The study encompasses a total of 891 piglets. The absolute weight gain and daily increase in growth were calculated from the weights on removal from the sows and release from the pens. The rearing period was ascertained using the weaning date and date of sale.

Results:
Serological Results:

The sampling of the piglets at the end of the rearing phase (24 positive results out of a total of 120 samples taken) proved that the test groups had been exposed to *Lawsonia intracellularis* during the rearing period.

Development of the Performance Parameters During the Rearing Period of the Piglets:

As can be seen from Table 1, the weaned weights at the start of the study differed significantly in favour of the vaccinated pigs, in spite of the random allocation of the piglets to the test groups.

TABLE 1

Performance of the piglets that received embedded vaccination, by comparison with the piglets treated with tylosin for 18 days

| | Vaccinated | Unvaccinated | Difference vaccinated − unvaccinated | p |
|---|---|---|---|---|
| n | 470 | 421 | | |
| weaned weight | 7.81 kg | 8.33 kg | −0.52 kg | <0.001 |
| sale weight | 30.23 kg | 29.26 kg | +0.97 kg | <0.01 |
| rearing period | 51.48 days | 52.9 days | −1.42 days | <0.05 |
| daily increase | 421 g | 404 g | +17 g | <0.001 |

At the end of the rearing period of the piglets that lasted on average 52.9 days (unvaccinated) or 51.48 days (vaccinated) the piglets treated by embedded vaccination weighed on average 0.97 kg more than the piglets treated with tylosin for 18 days in spite of their less favourable starting weight. This corresponds to a weight gain during the rearing period in the vaccinated animals which is 1.49 kg greater. The sale weights of the two groups differed highly significantly (p<0.001), the vaccinated piglets weighing 30.23 kg and the tylosin-treated piglets weighed 29.26 kg. The vaccinated piglets gained on average 421 g per day and thus differed highly significantly (p<0.001) from the tylosin-treated piglets, which on average gained 404 g per day.

TABLE 2

Rearing period of the piglets treated by embedded vaccination by comparison with piglets treated with tylosin for 18 days

| N | Vaccinated 470 | Unvaccinated 421 |
|---|---|---|
| Min. growth period | 31 days | 31 days |
| Max. growth period | 79 days | 96 days |

For a piglet producer or breeder, the maximum rearing period is also important, besides the absolute rearing period. The maximum rearing period crucially determines the time at which a pen can be vacated and hence cleaned, disinfected and reoccupied. The shortest time after which a piglet was sent on for fattening was identical at 31 days for both test groups (Table 2). However, there were significant differences in the maximum rearing period. Whereas the vaccinated piglets were kept for a maximum of 79 days, unvaccinated and tylosin-treated piglets occupied their pens for a maximum of 96 days (Table 2). Thus, the breeding pens containing the tylosin-treated groups were in some cases blocked for 17 days longer than pens containing vaccinated groups.

LITERATURE

1. Armbruster, G., Pelger, G.; Keffaber, K.; Armstrong, T. und Weatherford, J. (2004): Evaluation of Enterisol LI Ileitis vaccine and Tylan premix efficacy against porcine proliferative enteropathy in a challenge model. Proc 18th IPVS, S. 579.
2. Bornhorn, R. (2007): Wirksamkeit und Rentabilität einer Enterisol® Ileitis-Impfung über das Futter bei bereits teilweise infizierten Ferkelgruppen, Prakt Tierarzt, 3, 172-178.
3. Busch, M. E.; Jorsal, S. E.; Sloth, N. M.; Moeller, K.; Pedersen, A. O.; Dahl, J. (2000): The effect of Tylosin in low doses on the prevalence of Lawsonia intracellularis and the productivity in growing-finishing pigs. Proceedings 16th IPVS, 32.
4. Chouet, S.; Prieto, C.; Mieli, L.; Veenhuizen, M. F.; McOrist, S. (2003): Patterns of exposure to Lawsonia intracellularis infection on European pig farms. Veterinary Record. 152, 14-17.
5. Collins, A. M.; Van Dijk, M.; McOrist, S.; Love, R. J. (2000): Strategic medication and development of immunity to Lawsonia intracellularis. Proc 16th IPVS, S. 30.
6. Dritz, S. S.; Tokach, M. D.; Goodband, R. D.; Nelssen, J. L. (2002): Effects of administration of antimicrobials in feed on growth rate and feed efficiency of pigs in multisite production systems. JAVMA 220, 1690-1695.
7. EC Regulation 1831, (2003): Regulation (EC) No. 1831/2003 of the European Parliament and of the Council of 22 Sep. 2003 on additives for use in animal nutrition. Official Journal of the European Union, L268/29-L268/43.
8. Hardge, T.; Keller, C. H.; Steinheuer, R; Tessier, P. H.; Salleras, J. M.; Rubio, P.; Vestergaard, K.; Cluydts, G.; Ceccarelli, V.; Bugliesi, M.; Schippers, R.; Johnson, K.; Papatsas, J.; Eichin, E.; Rigat, J.;. Trela, T. (2006): Serological Prevalence of Lawsonia intracellularis across European pig herds. Proceedings. 19th IPVS, Copenhagen, 77. (2006).
9. Keller, C.; Ohlinger, V. F.; Nordengran, A. und Merza, M. (2004): A blocking. Elisa for the detection of antibodies against Lawsonia intracellularis. Proc. 18th IPVS, S. 293.
10. Kesl, L.; Saltzman, R.; Winkelmann, N.; Armbruster, G.; Pelger, G.; Kefaber, K.; Armstrong, T. und Weatherford. T. (2004): Tylan Premix and Enterisol LI Ileitis vaccine evaluations in a Lawsonia intracellularis challenge model. Proc. AASV, 139-40.
11. Kroll, J. J.; Roof, M. B.; Hoffman, L. J.; Dickson, J, S.; Harris, D. L. (2005): Proliferative enteropathy: a global enteric disease of pigs caused by Lawsonia intracellularis. Anim. Health Res. Rev., vol. 6, no. 2, 173-197.
12. Paradis, M. A.; Pauling, G. E.; Brennan, J.; Winkelman, N. L.; Bagg, R. N.; Dick, C. P.; Wilson, J. (2004): Evaluation of tylosin tartrate in drinking water for treatment of porcine proliferative enteropathy (Ileitis). J Swine Health Prod 12 (4), 176-181.
13. Steinheuer, R.; Bubikat, A.; Hardge, T. und Keller, C. (2007): Feldstudie zur Verbreitung sowie zu Einflussfaktoren auf die Seroprävalenz von Lawsonia intracellularis. Tierärztl Umschau, 62, 261-268.
14. Sub, D. K.;. Lym, S. K.; Bae, Y. C.; Lee, K. W.; Choi, W. P.; Song, J. C. (2000): Detection of Lawsonia intracellularis in diagnostic specimens by one-step PCR. J Vet Sci. 1, 33-37.
15. Thaker, M. Y. C. und Bilkei, G. (2006): Vergleich der Wirkung einer oralen Vakzination oder verschiedener antibiotischer Prophylaxen gegen Lawsonia intracellularis verursachte Verluste in einem Schweinebestand mit hohem Erregerdruck durch porcine proliferative Enteropathie (PPE). Tierärztl. Umschau 61, 372-376.
16. Tzika, E. D.; Alexopoulos, C.; Tassis, P. D.; Kyriakis, C. S. und Kyriakis S. C. (2004): Field evaluation of the effect of in-feed lincomycin for the control of Ileitis in growing pigs. Proc. 18th IPVS, 31-32 (2004).
17. Veenhuizen, M. F.; Mowrey, D. H.; Moore, G. M. und Watkins, L. E. (1998): Evaluating a natural outbreak of porcine proliferative enteropathy and treatment with tylosin in the growth-finish phase. J Swine Health Prod. 6 (2), 67-72.
18. Walter, D.; Knittel, J.; Schwartz, K.; Kroll, J. und Roof, M. (2000): Effectiveness of Tiamulin in feed for control and treatment of porcine proliferative enteropathy (Ileitis) due to Lawsonia intracellularis infection. Proc. 16th IPVS, 75.
19. Wendt, M., D. Brandt, U. Kaim und W. Baumgartner (2006): Effects of subclinical Lawsonia intracellularis infection studied from weaning to slaughter. Proc. 19th IPVS.
20. Winkelman, N.; Hoick, J. T.; Turner, V. und Luempert, L. (2000): Therapeutic impact of Econor® (Valnemulin Hydrochloride) on the development of porcine proliferative enteritis when supplied simultaneous to a Lawsonia intracellularis challenge. Proc. 16th IPVS, 70.

The invention claimed is:

1. A method of increasing weight gain and growth of weaned piglets comprising administering a live attenuated Lawsonia intracellularis vaccine when the piglets are about four weeks of age and administering tylosin antibiotic effective against Lawsonia intracellularis for a period of 18 to 21 days starting at day 3 after the administration of the live attenuated Lawsonia intracellularis vaccine.

2. A method of reducing the maximum rearing period of piglets comprising administering a live attenuated Lawsonia intracellularis vaccine when the piglets are about four weeks of age and administering tylosin antibiotic effective against Lawsonia intracellularis for a period of 18 to 21 days starting at day 3 after the administration of the live attenuated Lawsonia intracellularis vaccine.

3. The method of claim 1, wherein said tylosin antibiotic is administered in an amount of 10 to 50 mg/kg of body weight of the piglets.

4. The method of claim 2, wherein said tylosin antibiotic is administered in an amount of 10 to 50 mg/kg of body weight of the piglets.

5. The method of claim 1, wherein the live attenuated Lawsonia intracellularis vaccine induces Lawsonia intracellularis -specific antibodies in the piglets.

6. The method of claim 2, wherein the live attenuated Lawsonia intracellularis vaccine induces Lawsonia intracellularis -specific antibodies in the piglets.

* * * * *